(12) United States Patent
Linninger

(10) Patent No.: US 8,457,733 B2
(45) Date of Patent: Jun. 4, 2013

(54) MONITORING AND CONTROLLING HYDROCEPHALUS

(76) Inventor: Andreas Linninger, Oak Park, IL (US)

(*) Notice: Subject to any disclaimer, the term of this patent is extended or adjusted under 35 U.S.C. 154(b) by 708 days.

(21) Appl. No.: 12/305,484

(22) PCT Filed: Jul. 2, 2007

(86) PCT No.: PCT/US2007/015368
§ 371 (c)(1),
(2), (4) Date: Feb. 8, 2010

(87) PCT Pub. No.: WO2008/005440
PCT Pub. Date: Jan. 10, 2008

(65) Prior Publication Data
US 2010/0130884 A1 May 27, 2010

Related U.S. Application Data

(60) Provisional application No. 60/818,095, filed on Jun. 30, 2006, provisional application No. 60/899,243, filed on Feb. 2, 2007.

(51) Int. Cl.
*A61B 5/00* (2006.01)
(52) U.S. Cl.
USPC .......................................... 600/547
(58) Field of Classification Search
USPC ................................. 600/547, 561
See application file for complete search history.

(56) References Cited

U.S. PATENT DOCUMENTS

| 3,147,750 | A | 9/1964 | Fry |
| 6,248,080 | B1 | 6/2001 | Miesel et al. |
| 6,360,123 | B1 * | 3/2002 | Kimchi et al. ............... 600/547 |
| 2002/0052563 | A1 * | 5/2002 | Penn et al. .................. 600/561 |
| 2003/0045870 | A1 | 3/2003 | Madsen |

FOREIGN PATENT DOCUMENTS

| EP | 0670497 | 9/1995 |
| JP | 2000140092 | 5/2000 |
| WO | 0232335 | 4/2002 |

* cited by examiner

*Primary Examiner* — Max Hindenburg
(74) *Attorney, Agent, or Firm* — Nutter McClennen & Fish LLP; Konstantin Linnik

(57) ABSTRACT

Systems and methods for monitoring cerebral spinal fluid (CSF) based on electrical impedance measurements are disclosed. The systems can include an excitation source of alternating current (202), at least two sensor electrodes (212, 214) adapted for disposition within CSF in a ventricle of a subject's brain, and an impedance measuring device (204) electrically connected to the sensor electrodes (212, 214) to measure impedance of CSF. Methods for controlling hydrocephalus are also disclosed and such methods can include the steps of disposing an impedance sensor (902) within CSF in a ventricle of a subject's brain, measuring impedance of the CSF with the sensor (902), and withdrawing CSF when the impedance measurement is less than a threshold value.

22 Claims, 7 Drawing Sheets

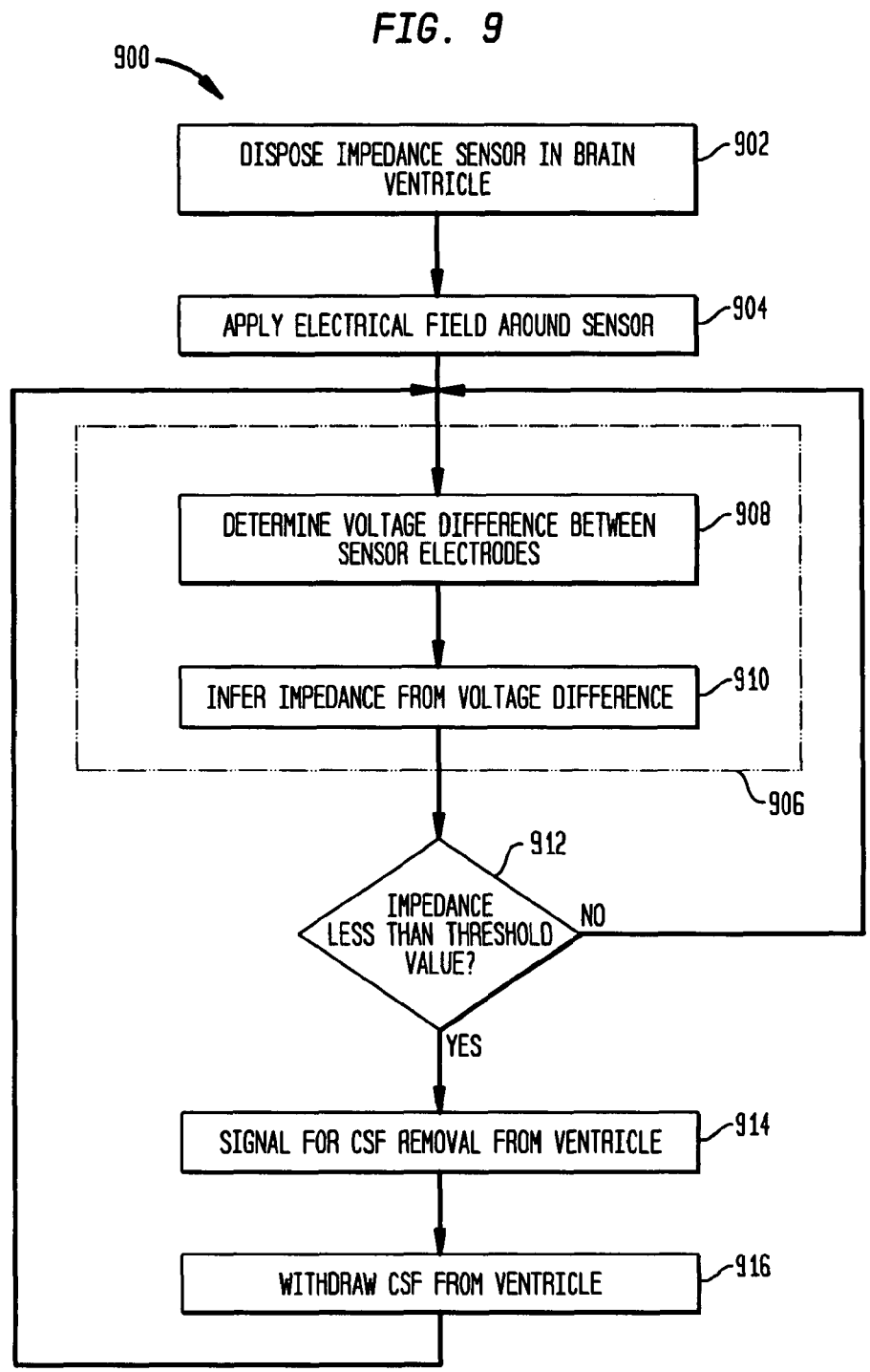

MONITORING AND CONTROLLING HYDROCEPHALUS

CROSS-REFERENCE TO RELATED APPLICATIONS

This application is a National Stage filing under 35 U.S.C. §371 of PCT/US2007/015368 filed on Jul. 2, 2007, which claims priority to U.S. Provisional Application Ser. No. 60/818,095 filed Jun. 30, 2006 and U.S. Provisional Application Ser. No. 60/899,243 filed Feb. 2, 2007.

STATEMENT REGARDING FEDERALLY SPONSORED RESEARCH OR DEVELOPMENT

This invention was made with government support under Grant No. EB004956 awarded by The National Institutes of Health. The government has certain rights in the invention.

BACKGROUND

The technical field of this invention concerns monitoring and controlling hydrocephalus.

Hydrocephalus is a neurological condition caused by the abnormal accumulation of cerebrospinal fluid (CSF) within ventricles, or cavities, of the brain. Hydrocephalus, which can afflict infants, children, and adults, arises when normal drainage of CSF in the brain becomes blocked in some way. Blockage of the flow of CSF consequently creates an imbalance between the rate at which CSF is produced by the ventricular system and the rate at which CSF is absorbed into the bloodstream. This imbalance increases pressure on the brain and causes the brain's ventricles to enlarge. Left untreated, hydrocephalus can result in serious medical conditions, including compression of the brain, atrophy of neural tissues, impaired blood flow, coma, and death.

Hydrocephalus may be treated by surgically inserting a shunt system to divert the flow of CSF from the ventricle to another area of the body, such as the peritoneum or another location in the body, where CSF can be absorbed. Typically, shunt systems remove excess CSF using a two-part catheter system that includes a ventricular catheter and a drainage catheter. The ventricular catheter can have a first end that is inserted into the skull of a patient and disposed within the ventricle of a patient, and a second end that is typically coupled to the inlet portion of the shunt valve. The first end of the ventricular catheter can contain multiple holes or pores to allow the CSF to enter the shunt system. At the other end of the shunt system, the drainage catheter has a first end that is attached to the outlet portion of the shunt valve and a second end that is configured to allow CSF to exit the shunt system for reabsorption into the blood stream.

Generally, the shunt valve, which can have a variety of configurations, is effective to regulate the flow rate of fluid through the shunt system. In some shunt valve mechanisms, the fluid flow rate is proportional to the pressure difference at the valve mechanism. These shunt valve mechanisms permit fluid flow only after the fluid pressure has reached a certain threshold level. Thus, when the fluid pressure is slightly greater than the threshold pressure level, the fluid flow rate is relatively low, but as the pressure increases, the fluid flow rate simultaneously increases. Typically, the shunt valve allows fluid to flow normally until the intracranial pressure has been reduced to a level that is less than the threshold pressure of the shunt valve, subject to any hysteresis of the device.

Some shunt valves allow external adjustment of the threshold pressure level at which fluid flow will commence. For example, the shunt valve can contain a magnetized rotor to control the pressure threshold of the valve. A physician can then use an external adjustment mechanism, such as a magnetic programmer, to adjust the pressure threshold of the shunt valve. However, these magnetized rotors can be unintentionally adjusted in the presence of a strong external magnetic field, such as during a magnetic resonance imaging (MRI) procedure. Unintentional adjustment of the pressure threshold could lead to either the overdrainage or underdrainage of CSF, which can result in dangerous conditions, such as subdural hematoma.

SUMMARY

Systems and methods for monitoring cerebral spinal fluid (CSF) based on electrical impedance measurements are disclosed. The systems can include an excitation source of alternating current, at least two sensor electrodes adapted for disposition within CSF in a ventricle of a subject's brain, and an impedance measuring device electrically connected to the sensor electrodes to measure impedance of CSF. Methods for controlling hydrocephalus are also disclosed and such methods can include the steps of disposing an impedance sensor within CSF in a ventricle of a subject's brain, measuring impedance of the CSF with the sensor, and withdrawing CSF when the impedance measurement is less than a threshold value.

Implementations of the invention can include one or more of the following features. The system can include a controller adapted to signal for withdrawal of CSF when the impedance measurement is less than a threshold value. The threshold value can reflect an impedance difference between CSF and tissue of the subject's brain. The system can further include at least four sensor electrodes adapted for disposition within CSF in a ventricle of a subject's brain. The system can further include a pressure measuring device adapted to measure pressure within the ventricle. The system can further include a controller adapted to signal for withdrawal of CSF when the pressure measurement is greater than a threshold value. The impedance measuring device can be adapted to measure a voltage drop between the sensor electrodes and to infer impedance from the voltage drop. The sensor electrodes can be separated by a distance in a range of about 10 mm to about 40 mm. The excitation source can be adapted to provide a frequency in the range of about 0.01 Hz to about 135 KHz. The alternating current can be about 100 µA. The system can further include at least two excitatory electrodes adapted for disposition with CSF in a ventricle of a subject's brain, for receiving alternating current from the excitation source, and for creating an electrical field extending around the sensor electrodes.

Implementations of the invention can include one or more of the following features. The method can further include measuring impedance by applying a time-varying electrical signal and measuring a voltage with the sensor. Measuring impedance can further include determining a voltage drop between at least two electrodes of the sensor. The method can further include measuring pressure in the ventricle and withdrawing CSF when the pressure measurement is above a threshold value. The method can further include applying an electrical field extending around the sensor. The threshold value can reflect an impedance difference between CSF and tissue of the subject's brain.

According to one aspect of the invention, a system includes an excitation source of alternating current, at least two sensor electrodes adapted for disposition within CSF in a ventricle of a subject's brain, a measuring device electrically connected to the sensor electrodes and adapted to measure impedance between the sensor electrodes, a CSF withdrawal mechanism, and a controller adapted to signal the CSF withdrawal mechanism to withdraw CSF from the ventricle when the impedance is less than a threshold value.

Implementations of the invention can include one or more of the following features. The system can further include a pressure measuring mechanism adapted to measure a pressure of CSF within the ventricle. The CSF withdrawal mechanism can be adapted to withdraw CSF from the ventricle when the pressure measurement is greater than a threshold value. The system can further include at least two excitatory electrodes adapted for receiving the alternating current and for disposition with CSF in a ventricle of a subject's brain. The CSF withdrawal mechanism can include a micro-pump. The threshold value can reflect an impedance difference between CSF and tissue of the subject's brain. The sensor electrodes can be separated by a distance in a range of about 10 mm to about 40 mm. The excitation source can be adapted to provide a frequency in the range of about 0.01 Hz to about 135 KHz. The alternating current can be about 100 μA. The measuring device can be adapted to measure a voltage drop between the sensor electrodes and to infer impedance from the voltage drop.

One or more of the following advantages can be provided by one or more aspects of the invention. Hydrocephalus can be treated by monitoring volume of CSF in a ventricle of a subject's brain and discharging an amount of CSF when the volume exceeds a certain amount. The volume can be monitored by measuring impedance of CSF in a brain ventricle and discharging CSF from the ventricle when the impedance drops below a threshold value, indicative of a desired ventricular volume typically predetermined by the subject's physician. Discharging excess CSF based on an impedance measurement does not or is less likely to depend on gravity, a subject's physical position, or a subject's exposure to magnetic fields such as those generated by MRI machines than other hydrocephalus treatments such as using pressure-based measurements in the brain to determine CSF discharge from a ventricle. In addition to using impedance-based measurements to discharge CSF, one or more other hydrocephalus treatments such as using pressure-based measurements to discharge CSF can also be used to further improve treatment.

Other advantages and features will become apparent from the following description and from the claims.

BRIEF DESCRIPTION OF THE DRAWINGS

FIG. 9 is a flowchart showing a process of monitoring and controlling hydrocephalus.

DETAILED DESCRIPTION

Figure 1:
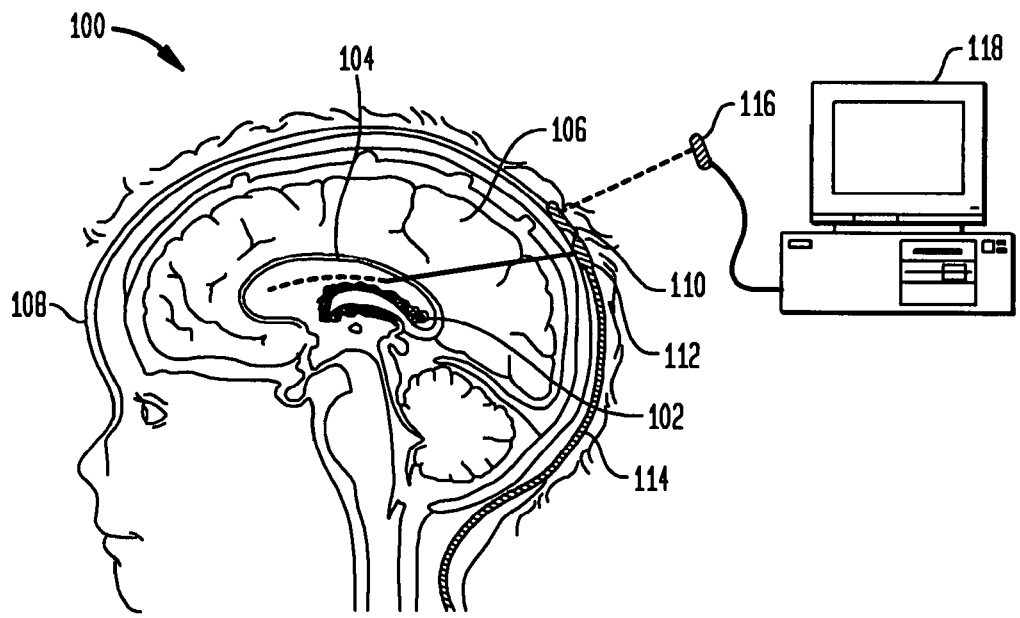
FIG. 1 is a schematic diagram of a CSF volume monitoring and control system according to the invention.

Referring to FIG. 1, a CSF volume monitoring and control system 100 includes a volume sensor 102 disposed in CSF in a ventricle 104 of a brain 106 of a patient 108. The system 100 can monitor and control volume of CSF in the ventricle 104 by measuring impedance of the CSF with the sensor 102 and electrically communicating the impedance measurement to a controller such as a central processing unit (CPU) 110. The CPU 110 can determine whether the impedance measurement is less than a threshold impedance value. The threshold value reflects an impedance difference (and thus also a conductance difference) between CSF and tissue of the brain 106. The threshold value also reflects a threshold level below which volume of CSF in the ventricle 104 exceeds a set point, typically prescribed by a physician. If the impedance measurement is less than the threshold value, the CPU 110 can signal a micro pump 112 to remove excess CSF from the ventricle 104. The micro pump 112 can remove excess CSF from the ventricle 104 through a shunt tube 114 and into the patient's abdominal cavity or other suitable location (e.g., a vein).

The CPU 110 can include an antenna for telemetry and a battery re-chargeable via radiofrequency (RF) technology and transmit ventricle measurement data to a telemetry device 116. The telemetry device 116 can wirelessly receive data from the CPU 110 and record measurements of the patient's actual ventricle size in real-time. The telemetry device 116 can communicate the data to a processor 118 (e.g., a personal computer) which can store, analyze, and/or display the data in real-time.

In the embodiment shown in FIG. 1, certain elements are surgically implanted in the patient 108. The sensor 102 is disposed in CSF in a lateral ventricle 104. The CPU 110 is located in the subgaleal space between the skull and scalp of the patient 108. The micro pump 112 is placed in a burr hole formed by drilling, scraping, or otherwise creating a hole in the skull of the patient 108. The shunt tube 114 at one end is connected to the micro pump 112. In other embodiments one or more of the elements may be arranged in a different configuration.

Figure 2:
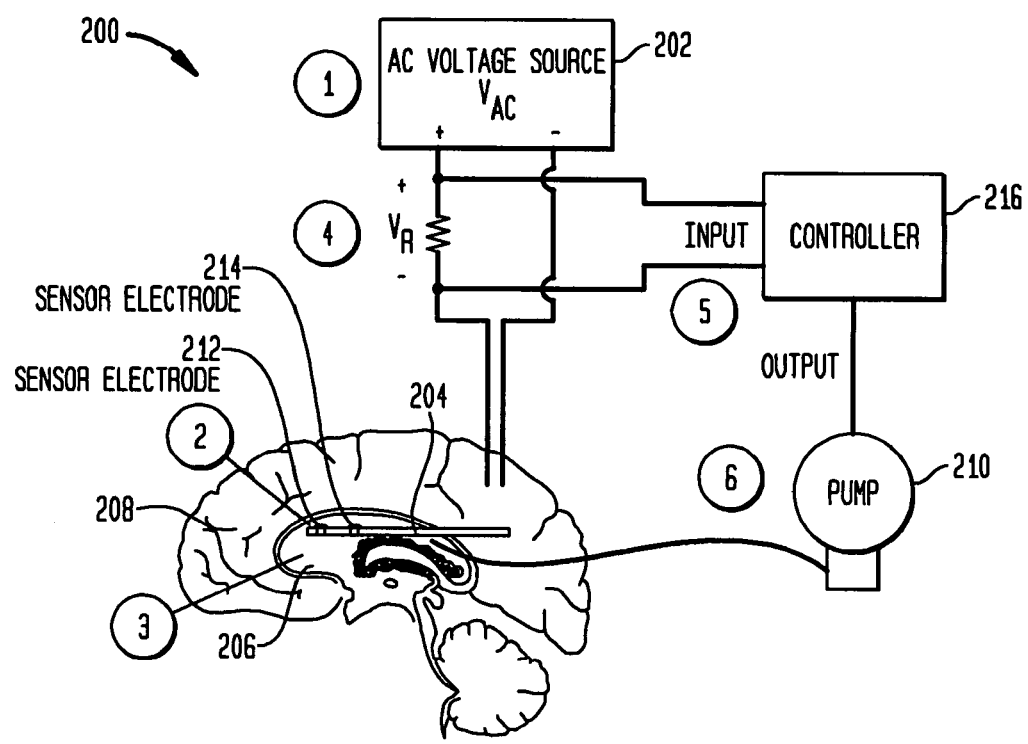
FIG. 2 is a another schematic diagram of a CSF monitoring and control system according to the invention further illustrating the electronic components.

Referring to FIG. 2, another embodiment of a CSF volume monitoring and control system 200 is shown. An excitation source such as an alternating current (AC) voltage source 202 can apply a time-varying electrical signal such as AC current to a sensor 204 disposed in CSF in a brain ventricle 206. When an alternating current is applied within a fluid-filled cavity such as the ventricle 206, the impedance of the fluid within the cavity corresponds to the volume of the fluid. The impedance can be inferred by measuring a voltage drop across a certain distance of the fluid-filled space. The relationship between measured volume of the fluid ($V_f$) and the fluid's impedance (Z) can be given as:

$$V_f = (\alpha) \cdot \left[\frac{1}{Z}\right]$$

Figure 3:
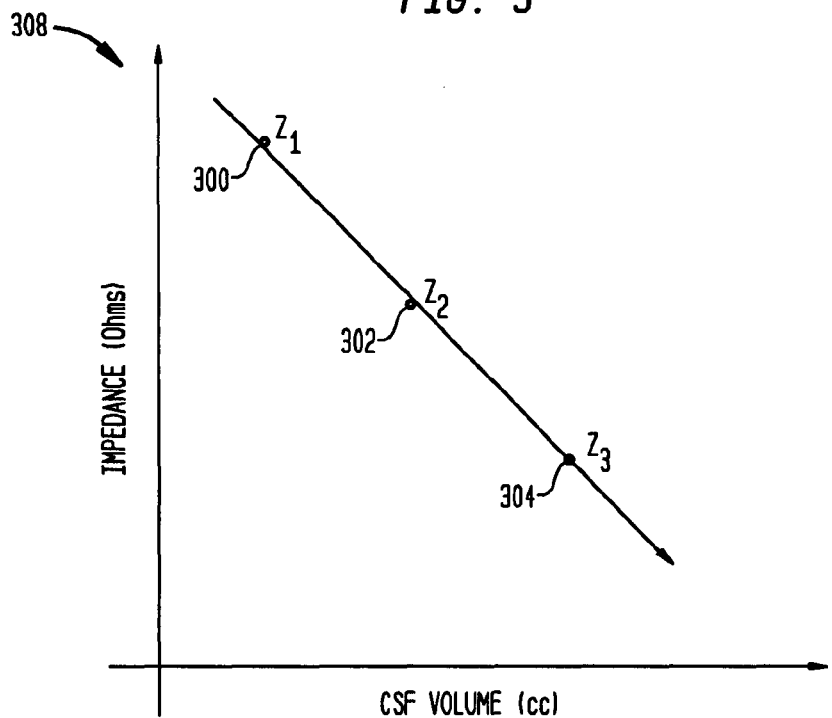
FIG. 3 is a graph plotting impedance versus volume.

Referring to FIG. 3, the constant $\alpha$ represents the slope of the tangent of measured impedance-volume values 300, 302, 304 as shown on an example graph 306 of impedance versus CSF volume.

Referring again to FIG. 2, if a CSF-filled cavity such as the ventricle 206 is surrounded by a tissue with sufficiently larger impedance (lower conductance) such as a brain tissue 208, then the measured impedance of the CSF in the ventricle 206 reading strongly correlates to the volume of CSF in the ventricle 206. Accordingly, a decrease in the impedance reading by the sensor 204 directly corresponds to an increase in the size of the ventricle 206 and vice versa.

The sensor 204 can electrically transmit its impedance readings to a controller 216. The controller 216 can determine if each of the impedance readings varies from a threshold impedance value, typically pre-programmed into the controller 216. If the impedance reading is greater than or equal to the threshold value, then the inference is that ventricular volume and the volume of CSF in the ventricle 206 are within acceptable limits. If the impedance reading is less than the threshold value, then the inference is that ventricular volume increased and there is excess CSF in the ventricle 206. The controller 216 can compute a CSF correction and transmit the CSF correction to a pump 210 in any manner compatible with the pump 210. The pump 210 may then remove an amount of CSF from the ventricle 206.

The pump 210 can include any pump or non-pump mechanism capable of being operated by the controller 216 and removing CSF from the ventricle 206, e.g., a micro pump or a shunt. If the pump 210 is a micro pump, it may have a pumping capacity of up to about 1.0 ml/min, preferably in the range of about 0.3 ml/min to 0.5 ml/min, and have a size less than about $4 \times 4 \times 1.5$ mm$^3$. The pump 210 may include a nano-pump.

In addition to controlling the amount of CSF in the ventricle 206 by monitoring impedance and hence CSF volume in the ventricle 206, hydrocephalus may be monitored and controlled using one or more additional treatments. For example, intracranial pressure (ICP) may also be monitored to control CSF levels. Multiple ICP monitoring and control systems are commonly available, and any may be used in the CSF volume monitoring and control system 200.

For example, the controller 216 may have the capability to control ICP in the ventricle 206. The controller 216 could receive ICP information from a pressure measuring device capable of measuring ICP within the ventricle. The pressure measuring device may signal the pump 210 to remove CSF from the ventricle 206 when the ICP measurement exceeds a certain threshold level. In another example, a pressure-controlled shunt could be used either as or in addition to the pump 210 in the CSF volume monitoring and control system 200 as a pressure measuring device.

By monitoring ICP in addition to ventricular volume, a patient can receive improved treatment. Some patients suffer from enlarged ventricles even though their ICP is normal (normal pressure hydrocephalus). Moreover, a weak correlation between the ICP and enlarged ventricles may be responsible for the overdraining or underdraining of CSF that often occurs with existing shunts. Overdrainage occurs due to an excessive removal of CSF and can lead to the collapse of ventricular spaces, slit ventricle system, and occlusion of ventricular catheters used to drain CSF. Underdraining occurs due to insufficient CSF drainage and can lead to larger ventricles and higher pressures than desired. Further, impedance measurements of CSF in the ventricle 206 are based indirectly on electric fields and are, often unlike ICP measurements, independent of outside forces like gravity, body position, and magnetic fields such as those produced in MRI procedures. In light of these shortcomings, it can be advantageous to measure the ventricular volume directly instead of relying exclusively on pressure-based correlation.

The source 202 may provide AC current at about 100 μA. Voltage from the source 202 can be in the range of about $\pm 0.1$-5 V with a frequency in the range of about 0.01 Hz to about 135 kHz to generate an electric field of about 0.0025 V/m in the fluid space between electrodes 212, 214. In this embodiment, one frequency is used to sample the sensor 204, but multiple frequencies may be used and may increase accuracy of impedance measurements. Higher excitation frequencies from the source 202 typically provide higher voltage values.

The controller 216 can include a re-chargeable battery with a capacity of, e.g., about 0.5 A·h operating at 2 V. One charge can last about one year, and with multiple re-charges possible, the battery could last the lifetime of the patient.

The sensor 204 includes two electrodes 212, 214 for measuring the impedance of the CSF in the ventricle 206. The electrodes 212, 214 are aligned linearly at a fixed distance. The fixed distance should allow for the electrodes 212, 214 to be immersed in CSF and should be large enough for the electrodes 212, 214 to be enveloped by the electrical field resulting from the current provided by the source 202. The fixed distance between the electrodes 212, 214 of the sensor 204 may be in the range of about 1 mm to about 40 mm or in smaller ranges of about 10 mm to about 40 mm, about 20 mm to about 25 mm, or about 1 mm to about 23 mm. The larger the distance between the electrodes 212, 214, typically the stronger the electrode potentials.

The sensor 204 may be disposed in CSF of the ventricle 206 at any alignment relative to the ventricle 206. However, a voltage drop between the electrodes 212, 214 can be more accurately measured and the resulting data can have smaller error if CSF is introduced to the ventricle 206 at an axis perpendicular to the sensor 204 rather than aligned parallel to CSF introduction. The sensor 204 can be positioned stereotactically in the ventricle 206.

The sensor 204 may be made of any material capable of measuring impedance in the ventricle 206. Examples of materials include copper, gold, stainless steel, titanium, silver, and platinum-iridium (Pl-Ir). Ideally, material such as Pl-Ir wire is used because it is MRI-compatible and bio-compatible for long term use.

The sensor 204 is ideally MRI compatible. A strong magnetic attraction between the MR scanner and the sensor 204 can cause the sensor 204 to reorient itself within the patient, causing injury. MRI compatibility also implies lack of distortion to MR images as well as negligible heat effects even in strong magnetic fields. Additional factors such as size, mass, and implantation site may also affect MRI compatibility of the sensor 204, usually requiring careful tests of the sensor 204 in the scanner field.

A protectant can be used to insulate and waterproof the interior of the electrodes 212, 214 to avoid fluid seepage and potential short-circuiting of the electrodes 212, 214. For example, silicone rubber may be used an a protectant due to its low immune and inflammatory response.

The sensor 204 is shown with two electrodes 212, 214 in the CSF volume monitoring and control system 200, but the sensor 204 may include more electrodes disposed within CSF in the ventricle 206. If the sensor 204 includes more than the two electrodes 212, 214, two (or more) of the additional electrodes may be excitatory electrodes capable of receiving a time-varying signal from the source 202 and creating an electrical field extending around the electrodes 212, 214. If the sensor 204 includes more than the two electrodes 212, 214, more than one impedance measurement may be made by the sensor 204 between different ones of the electrodes, communicated from the sensor 204 to the controller 216, analyzed by the controller 216, and/or communicated from the controller 216 to a processing unit outside the patient's body.

The sensor 204 can make impedance measurements automatically. For example, the controller 216, e.g., a data gathering device integrated in or otherwise in electronic communication with the controller 216, can gather a voltage drop signal between the electrodes 212, 214.

Measurements can be taken at the sensor 204 at any sampling rate, i.e., four readings per second or one reading every five seconds. The sensor 204 can store the impedance measurements and transmit the measurements to the controller 216 at any transmission rate, e.g., at a rate equal to the sampling rate.

Calibration of the sensor 204 may be necessary to adjust for specific conditions unique to an individual patient, e.g., individual variations in CSF composition, tissue conductance, and shapes. Calibration concerns the relationship between a voltage drop between the electrodes 212, 214 and an absolute volume of the ventricle 206. A calibration approach adjusts for conditions of an individual patient and involves comparison of actual sensor readings to an accurate independent measurement.

Figure 4:
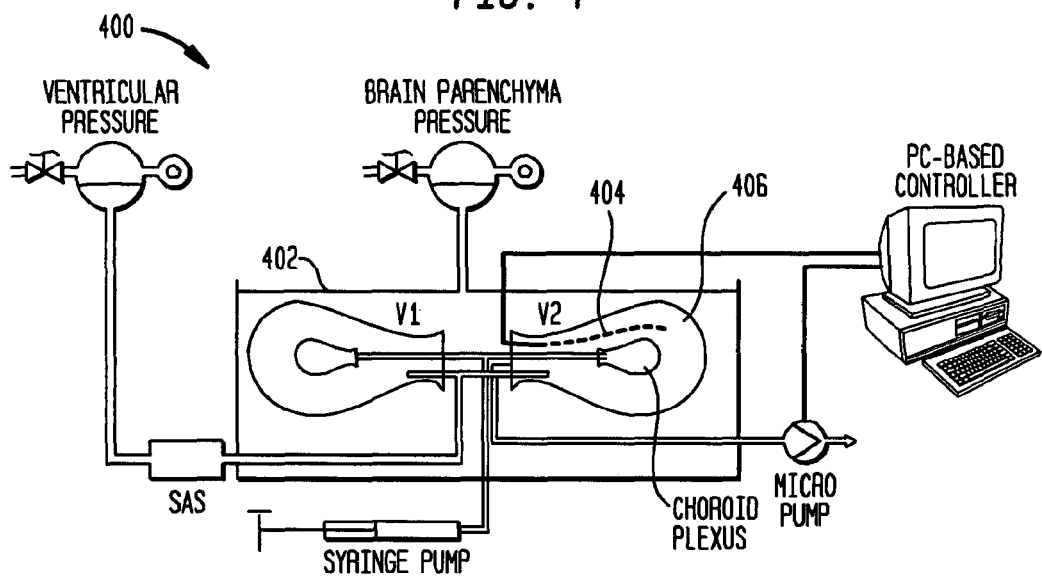
FIG. 4 is a schematic of a sensor calibration system.

Referring to FIG. 4, one example of a calibration approach includes comparative calibration setup 400 using a beaker 402. Specific properties of a sensor 404 may be inferred by submerging the sensor 404 in a complex shaped object 406 filled with CSF or a CSF-simulating fluid. The voltage drop measured in the complex ventricular shape 406 can be compared to measurements obtained in a reference beaker. The comparison can show whether the measurement in the "blind" experiment in complex geometry equals the voltage drop in the beaker.

Another example of a calibration approach includes deducing electrolytic properties of CSF by electric circuit simulations. When modeling a CSF-filled cavity as a network of generalized resistors, capacitors and impedances, the apparent properties of the fluid can be discovered by tuning the electric elements representing the fluid until the measured voltage drops for different volumes agree with the simulation. In a first approximation, resistance and conductance of the elements can be equated to the apparent fluid properties.

Another example of a calibration approach includes using precise MRI ventricular volume measurements to calibrate a sensor reading. This approach can use a geometric reconstruction of patient-specific brain images. Computational tools can be used for the accurate geometric reconstruction of patient-specific brain geometries for the simulations of CSF flow dynamics in normal and hydrocephalic patients. Curvilinear coordinate systems are introduced to minimize discretization errors in the transport equations for rendering complex and distorted geometries such as the human brain.

Referring again to FIG. 2, the controller 216 may infer impedance from some or all of the measurements received from the sensor 204. For example, the controller 216 may store all of the measurements received from the sensor 204 for transmission to a processing unit outside the patient's body but may only compute impedance on a sampling of the measurements.

The ventricular system of the brain is composed of four different communicating cavities that are connected to one another through narrow passage ways. The sensor 204 measures only the volume expansion of the ventricle 206 in which it is placed, not the entire volume of the connected cavities. Thus, if the sensor 204 communicates an impedance drop to the controller 216, and the controller 216 signals the pump 210 to remove CSF from the ventricle 206, it is because excess CSF exists in that ventricle 206 (excess CSF may or may not exist elsewhere in the brain).

Figure 5:
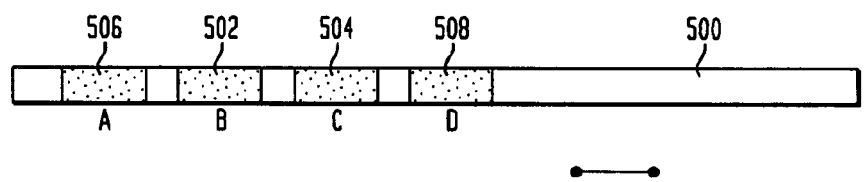
FIG. 5 is an inductive volume sensor.

Referring to FIG. 5, an embodiment of an inductive volume sensor 500 includes inner electrodes 502, 504 and outer electrodes 506, 508. The inner electrodes 502, 504 are situated to be between an alternating electric field generated by the outer electrodes 506, 508. Impedance is measured in the form of a voltage drop between inner electrodes 502, 504. The voltage drop is proportional to the volume of an electric fluid (e.g., CSF) around the inner electrodes 502, 504.

The sensor 500 can be of any shape or size. In this embodiment, the sensor 500 is a cylindrical rod with straight ends, although the sensor 500 may have any configuration, e.g., curved ends, rectangular rod, etc. The inner and outer electrodes 502, 504, 506, 508 can be assembled in various design configurations, e.g., a linear arrangement as shown on the sensor 500. Each of the electrodes 502, 504, 506, 508 can be about 1 mm in length. Examples of sensors that may be adapted for use as the sensor 500 include deep brain stimulation mechanisms such as those sold by Medtronic in the Activa Therapy System.

The outer electrodes 506, 508 may generate the electric field around the inner electrodes 502, 504 by, for example, receiving a time-varying signal such as an alternating current from an excitation source. The voltage at the outer electrodes 506, 508 should be below the water limit window (−0.6V to +0.8 V) to avoid hydrolysis when the outer electrodes 506, 508 are disposed in CSF.

Figure 6:
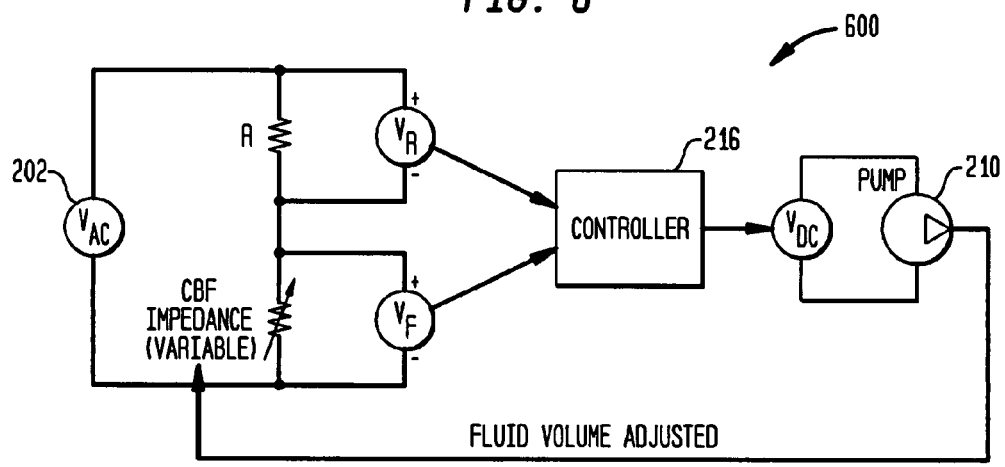
FIG. 6 is a measurement and control system circuit.

Referring to FIG. 6, a measurement and control system circuit 600 shows an example of the CSF volume monitoring and control system 200 in FIG. 2. Although the circuit 600 is described with reference to elements included in the example CSF volume monitoring and control system 200, this or a similar system, including the same, more, or fewer elements, reorganized or not, may be used to monitor and control ventricular volume in another, similar system.

The source 202 generates alternating current used to measure impedance of CSF by inferring the impedance from a fluid voltage ($V_F$). $V_F$ is transmitted to the controller 216 for comparison with a reference voltage ($V_R$). In the circuit 600, $V_R$ is shown as an input to the controller 216, but $V_R$ may be pre-programmed into the controller 216.

The controller 216 determines whether $V_F$ is less than $V_R$. If $V_F$ is less than $V_R$, then the controller 216 can signal the pump 210 with a direct current voltage ($V_{DC}$). The value of $V_{DC}$ can indicate to the pump 210 how much CSF to remove. For example, the value of $V_{DC}$ may trigger pumping for a certain length of time or signal pumping of a certain volume of CSF measured by the pump 210 as CSF flows through it. In making the $V_F$ versus $V_R$ determination, the controller 216 infers impedance from the voltage values and uses the impedance measurement to determine whether and how to signal the pump 210.

Figure 7:
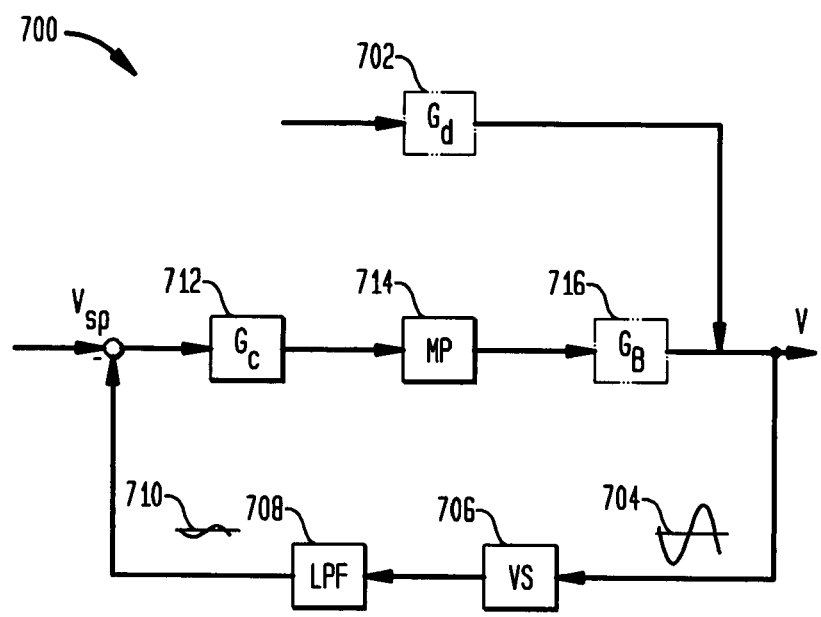
FIG. 7 is a block diagram of a feedback control loop.

Referring to FIG. 7, a block diagram of an example feedback control loop 700 shows a configuration of elements that can be used in a ventricular volume monitoring and control system. An excitation source or disturbance 702 electrically communicates a signal (i.e., alternating current) in the form of a wave 704 to a volume sensor 706 disposed in CSF of a brain ventricle. In the presence of an electrical field generated by the wave 704, the sensor 706 can make an impedance measurement indicating ventricular volume. The impedance measurement can pass through a low pass filter 708 to correct for possible error (e.g., detected pulsations from blood) before being electrically communicated as a filtered wave 710 to a controller 712. The low pass filter 708 may have a time constant of about 100,000 s ($\tau_f$=100,000 seconds) and receive a signal from the sensor 706 with a frequency of about 1 Hz.

The controller 712 analyzes the filtered wave 710 by comparing it with a threshold impedance value indicating an acceptable boundary limit of CSF volume in the ventricle including the sensor 706. The controller 712 can use, for example, a bang-bang control algorithm, a PI controller, or a P controller to determine a correction from an actual ventricular volume as indicated by the measured impedance to a desired ventricular volume as indicated by the threshold value. The threshold value typically indicates an impedance level below which CSF should be drained from the ventricle, but the threshold value may indicate an upper limit impedance level, with the controller's analysis appropriately adjusted. The correction may reflect the desired ventricular volume or a volume less than the desired ventricular volume.

The controller 712 electrically communicates a signal indicating the correction to a micro-pump 714. Based on correction data received from the controller 712, the micro-pump 714 can remove an amount of CSF from the ventricle including the sensor 706. The micro-pump 714 can electrically communicate a signal through a process transfer function 716. The output of the process transfer function 716 can be electrically communicated to the sensor 706.

Figure 8:
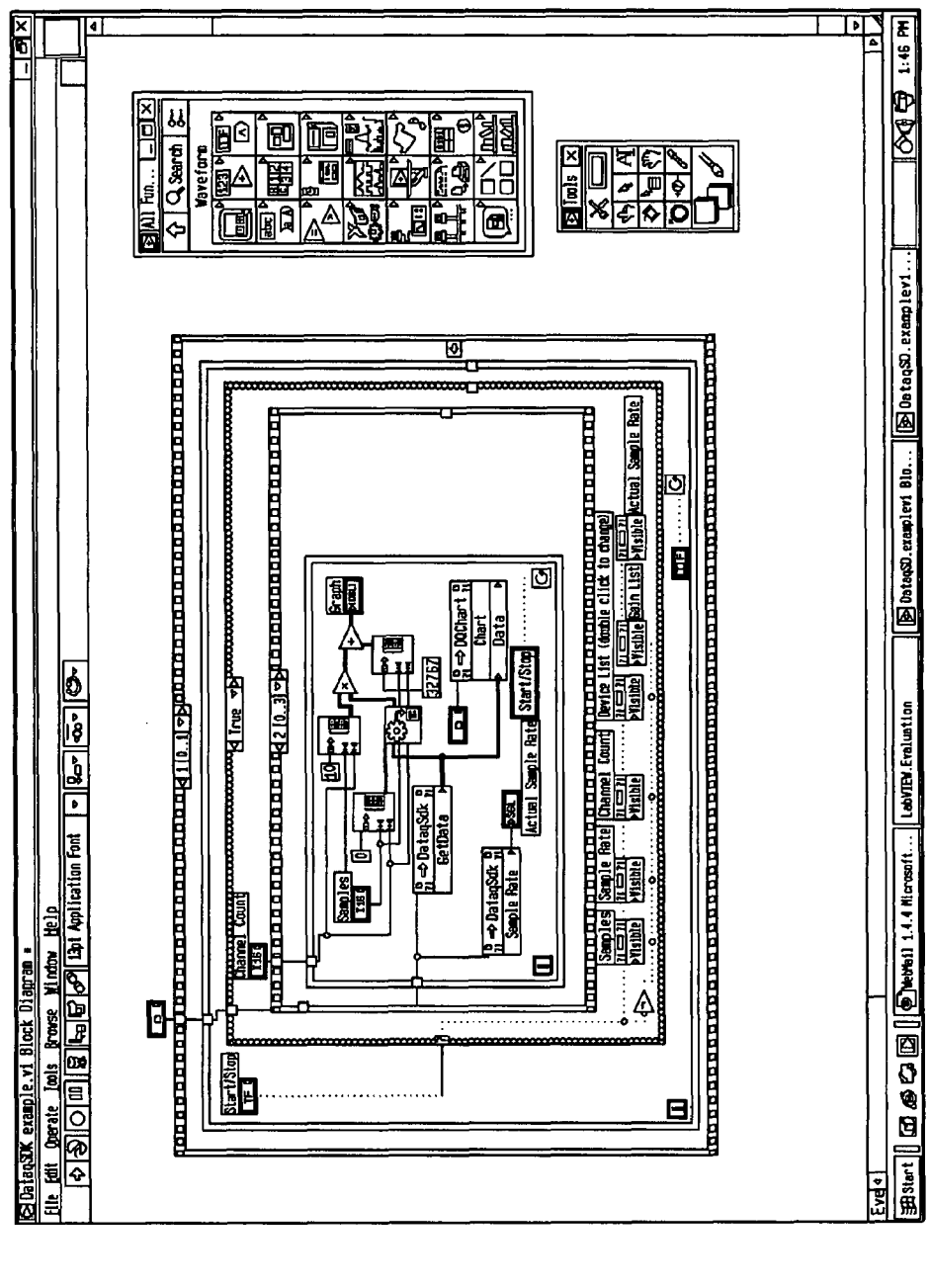
FIG. 8 is an active control screen.

Referring to FIG. 8, an example active control screen 800 shows a schematic that may be used in monitoring ventricular volume. A user may view, manipulate, and analyze data displayed on the screen 800 such as a sampling rate of a sensor disposed in CSF of a brain ventricle, measured impedance values, and an impedance threshold value. Data on the screen 800 can be obtained from the sensor, e.g., wirelessly downloaded from a controller in communication with the sensor. The user may also be able to view and create analyses of the data on the screen 800, e.g., tables and graphs.

The screen 800 is not limited to any particular layout or configuration. For example, manipulation tools such as pull-down menus, tabs, buttons, selection boxes, and scrollbars can be implemented using any similar type of manipulation tool. In another example, graphs can be presented in any graph format (e.g., bar, line, pie, etc.) and with any orientation (e.g., with horizontal or vertical bars). Furthermore, two or more screens may be combined and presented on a single screen and one screen may be divided into two or more screens. There may also be additional screens.

Users may manipulate the screen 800 in any way, e.g., using a mouse, a touch screen, a stylus, keyboard commands, etc. For example, a user may move his or her mouse pointer over an icon and click on the icon to access a particular functionality.

Referring to FIG. 9, a flowchart shows an example of a CSF volume monitoring and control process 900. The steps described with reference to FIG. 9 can be implemented in a variety of ways and may include one or more additional steps or steps within those described.

In the process 900, an impedance sensor is disposed 902 in CSF in a patient's brain ventricle. The sensor includes at least two electrodes between which impedance of the CSF may be measured. An electrical field is applied 904 around the sensor so impedance of the CSF can be measured 906 with the sensor. The electrical field may be applied 904 via an excitation source supplying the sensor with a time-varying signal, e.g., alternating current.

Measuring 906 impedance includes determining 908 a voltage difference between the at least two electrodes of the sensor. Impedance can be inferred 910 from the measured voltage difference. The measured impedance is compared 912 with a threshold impedance value, the threshold impedance value indicating an impedance level below which an excess of CSF exists in the ventricle including the sensor. If the measured impedance is equal to or greater than the threshold value, then no action is taken to trigger removal of CSF from the ventricle. If the measured impedance is less than the threshold value, then a mechanism capable of removing CSF from the ventricle is signaled 914 to remove CSF from the ventricle. CSF is then withdrawn 916 from the ventricle.

The process 900 continually runs from determining 908 the voltage difference and comparing 912 the measured impedance with the threshold value and taking further action as necessary.

Other embodiments are within the scope of the following claims.

The invention claimed is:

1. A system for monitoring cerebral spinal fluid (CSF) volume in a ventricle of a subject's brain comprising:
    an excitation source of alternating current,
    at least two sensor electrodes adapted for disposition within CSF in the ventricle of the subject's brain, and
    an impedance measuring device electrically connected to the sensor electrodes to measure impedance of CSF to measure CSF volume in the ventricle of the subject's brain.

2. The system of claim 1 wherein the system further comprises a controller adapted to signal for withdrawal of CSF when the impedance measurement is less than a threshold value.

3. The system of claim 2 wherein the threshold value reflects an impedance difference between CSF and tissue of the subject's brain.

4. The system of claim 1 wherein the system further comprises at least four sensor electrodes adapted for disposition within CSF in the ventricle of the subject's brain.

5. The system of claim 1 wherein the impedance measuring device is adapted to measure a voltage drop between the sensor electrodes and to infer impedance from the voltage drop.

6. The system of claim 1 wherein the sensor electrodes are separated by a distance in a range of about 10 mm to about 40 mm.

7. The system of claim 1 wherein the excitation source is adapted to provide a frequency in the range of about 0.01 Hertz to about 135 kHertz.

8. The system of claim 1 wherein the alternating current is about 100 µA.

9. The system of claim 1 wherein the system further comprises at least two excitatory electrodes adapted for disposition with CSF in a ventricle of a subject's brain, for receiving alternating current from the excitation source, and for creating an electrical field extending around the sensor electrodes.

10. A method for controlling hydrocephalus in a subject's brain comprising:
    disposing an impedance sensor within cerebral spinal fluid (CSF) in a ventricle of the subject's brain,
    measuring impedance in the ventricle with the impedance sensor to measure volume of the CSF in the ventricle, and
    withdrawing CSF when the impedance measurement is less than a threshold value.

11. The method of claim 10 wherein the step of measuring impedance further comprises applying a time-varying electrical signal and measuring a voltage with the sensor.

12. The method of claim 10 wherein the step of measuring impedance further comprises determining a voltage drop between at least two electrodes of the sensor.

13. The method of claim 10 further comprising applying an electrical field extending around the sensor.

14. The method of claim 10 wherein the threshold value reflects an impedance difference between CSF and tissue of the subject's brain.

15. A system for monitoring cerebral spinal fluid (CSF) volume in a ventricle of a subject's brain comprising:
    an excitation source of alternating current, at least two sensor electrodes adapted for disposition within the CSF in the ventricle of the subject's brain, a measuring device electrically connected to the sensor electrodes and adapted to measure impedance between the sensor electrodes to measure CSF volume, a CSF withdrawal mechanism, and a controller adapted to signal the CSF withdrawal mechanism to withdraw CSF from the ventricle when the impedance is less than a threshold value.

16. The system of claim 15 wherein the system further comprises at least two excitatory electrodes adapted for receiving the alternating current and for disposition with CSF in a ventricle of a subject's brain.

17. The system of claim 15 wherein the CSF withdrawal mechanism includes a micro-pump.

18. The system of claim 15 wherein the threshold value reflects an impedance difference between CSF and tissue of the subject's brain.

19. The system of claim 15 wherein the sensor electrodes are separated by a distance in a range of about 10 mm to about 40 mm.

20. The system of claim 15 wherein the excitation source is adapted to provide a frequency in the range of about 0.01 Hz to about 135 kHz.

21. The system of claim 15 wherein the alternating current is about 100 µA.

22. The system of claim 15 wherein the measuring device is adapted to measure a voltage drop between the sensor electrodes and to infer impedance from the voltage drop.

* * * * *